United States Patent [19]

Bancsi et al.

[11] Patent Number: 5,226,900

[45] Date of Patent: Jul. 13, 1993

[54] CANNULA FOR USE IN DRUG DELIVERY SYSTEMS AND SYSTEMS INCLUDING SAME

[75] Inventors: Joseph A. Bancsi, Vernon Hills; Charles Eller, Antioch; Thomas A. Fowles, McHenry, all of Ill.; Brian J. Gorman, Lake Geneva, Wis.; Terrance J. Hebron, Antioch, Ill.; Charles Jersild, Vernon Hills, Ill.; Donald A. Jess, Fox Lake, Ill.; Joseph C. T. Wong, Lake Villa, Ill.; Ray W. Wood, Elkhorn, Wis.

[73] Assignee: Baxter International Inc., Deerfield, Ill.

[21] Appl. No.: 924,262

[22] Filed: Aug. 3, 1992

[51] Int. Cl.$^5$ ............................................. A61B 19/00
[52] U.S. Cl. ................................. 604/411; 604/414; 604/905
[58] Field of Search ..................... 604/83–88, 604/201–206, 403–416, 905

[56] References Cited

U.S. PATENT DOCUMENTS

| | | |
|---|---|---|
| 4,412,573 | 11/1983 | Zdeb . |
| 4,537,593 | 8/1985 | Alchas . |
| 4,576,211 | 3/1986 | Valentini et al. ............... 604/201 X |
| 4,768,568 | 9/1988 | Fournier et al. ............... 604/905 X |
| 4,798,605 | 1/1989 | Steiner et al. ................. 604/411 |
| 4,804,366 | 2/1989 | Zdeb . |
| 4,834,152 | 5/1989 | Howson et al. ............... 604/414 X |
| 4,850,978 | 6/1989 | Dudar et al. . |
| 5,049,129 | 9/1991 | Zdeb et al. . |

OTHER PUBLICATIONS

Becton Dickinson, "NO-KOR TM Admix Needle Eliminates the Medication Waste and Patient Risk Associated with Coring", 1986.

*Primary Examiner*—John D. Yasko
*Attorney, Agent, or Firm*—Paul E. Schaafsma; Amy L. H. Rockwell; Paul C. Flattery

[57] ABSTRACT

The present invention provides an improved cannula that can be used to reconstitute powdered drugs in a drug delivery system. Furthermore, the present invention provides a cannula and drug delivery system incorporating same. To this end, the present invention provides a cannula structure for use in a reconstitution device for reconstituting a powdered drug comprising a cannula having a first end and a second end, and defining a channel in an interior thereof between the first and second ends. The first end is closed and includes a member for piercing a septum. The cannula includes at least two slots providing fluid communication between the channel and an exterior of the cannula. The slots are located in juxtaposition to the first end and have a width, as measured along a length of the cannula, that is less than a length, as measured around the cannula. The slots also have a minimum projected area equal to or greater than the cross-sectional area of the channel.

23 Claims, 3 Drawing Sheets

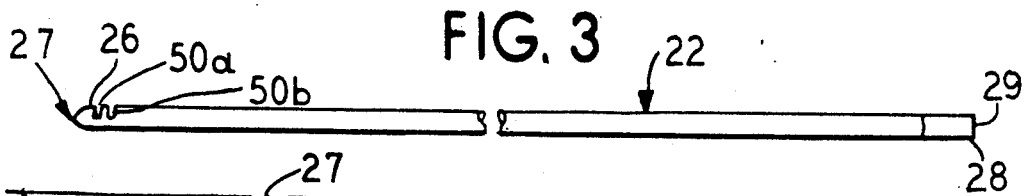
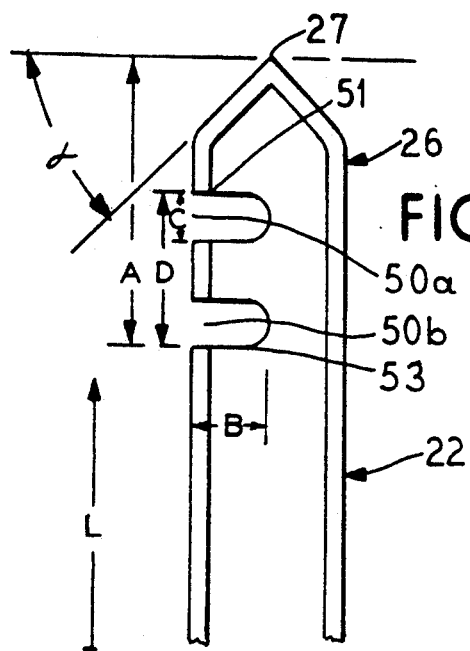
FIG. 6
AMPICILLIN 1 GRAM
NORMAL BEVEL NEEDLE
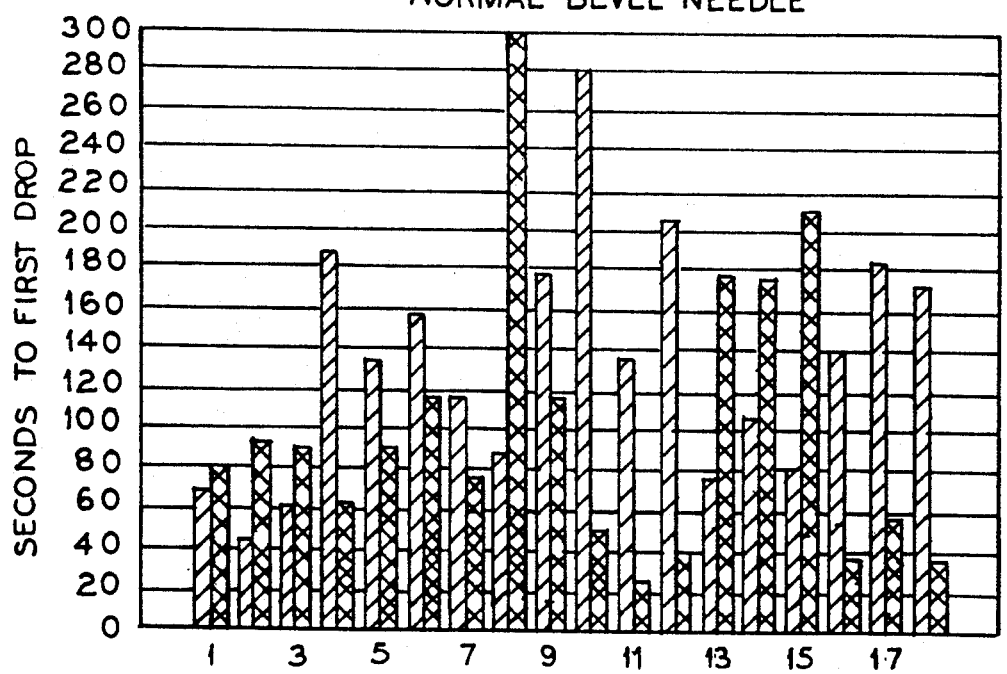

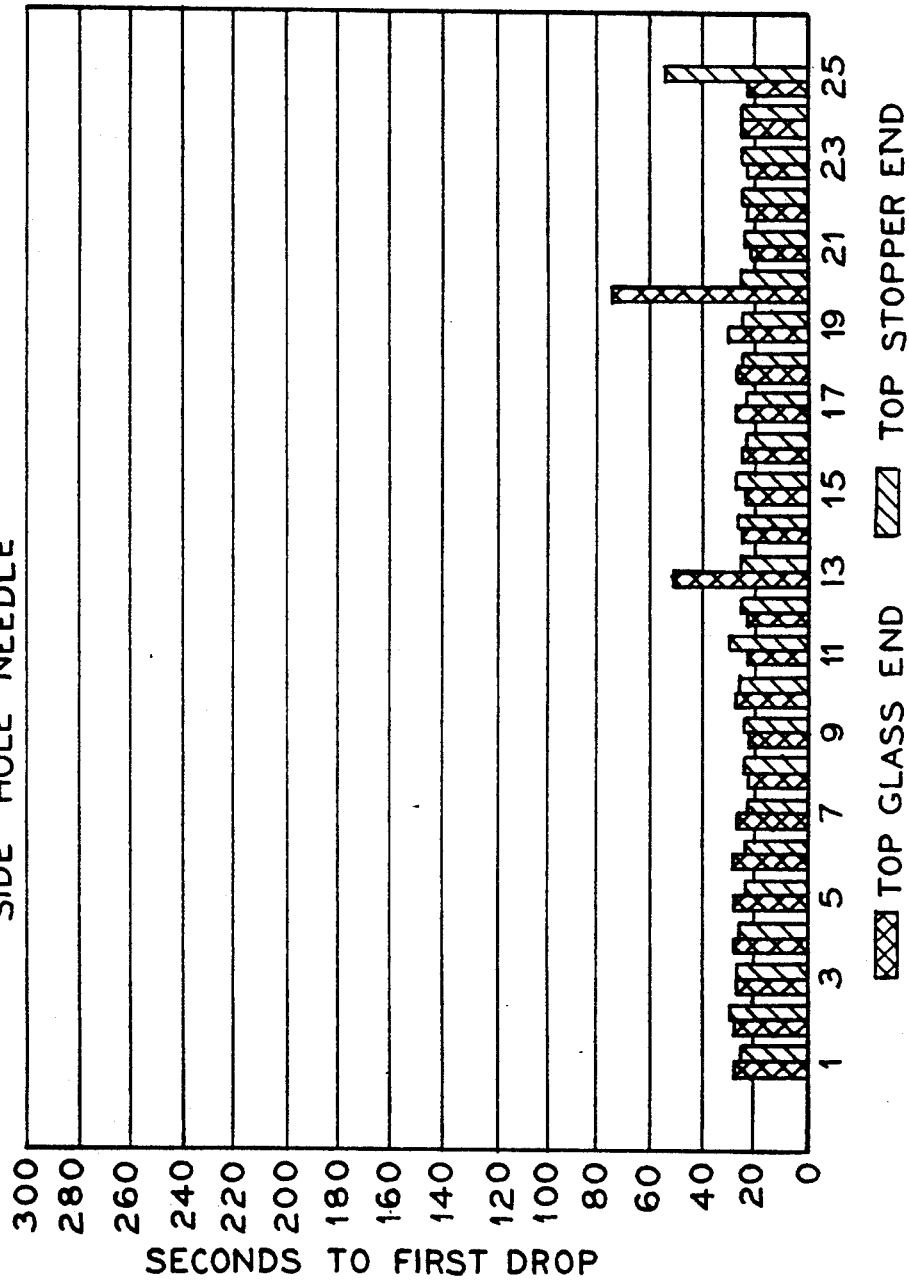

CANNULA FOR USE IN DRUG DELIVERY SYSTEMS AND SYSTEMS INCLUDING SAME

BACKGROUND OF THE INVENTION

The present invention relates generally to cannulas. More specifically, the present invention relates to cannulas for use in systems for delivering a beneficial agent to a patient or into a system for later delivery to a patient.

Pointed cannulas for use with injection sites have been known for use in the medical arena. Such cannulas can be utilized to access a medicament contained within a container or to create a fluid flow path within a housing. An example of an injection site usable with a piercing cannula is disclosed in U.S. Pat. No. 4,412,573.

Within a housing, to create a fluid flow path, a pointed cannula is utilized that is forced through a septum to create a flow path within the housing. Injection sites, however, which are utilized on a repetitive basis can be damaged by repetitive piercing by a sharp cannula. This damage, known as coring or laceration, can result in a subsequent leakage within the housing. As set forth in detail below, other disadvantages may exist with respect to pointed cannulas when they are used in drug delivery systems.

U.S. Pat. No. 4,537,593 discloses an allegedly non-coring self-venting needle assembly for use in the transfer of liquid to or from a container. The shaft of the needle includes a planar portion terminating in an edge and an aperture aligned with the edge to allow liquid to exit the shaft of the needle.

For many applications, drugs may be mixed with a diluent before being delivered, for example, intravenously, to a patient. The diluent may be, for example, a dextrose solution, a saline solution, or even water. To this end, many drugs are supplied in powder form and packaged in glass vials or ampules. Other drugs, such as chemotherapy drugs, are packaged in glass vials or ampules in a liquid state.

Powdered drugs may be reconstituted by utilizing a syringe to inject liquid into a vial for mixing; the syringe eventually withdrawing the mixed solution from the vial. When a drug must be diluted before delivery to a patient, the drug is often injected into a container of diluent after it is reconstituted, where the container can be connected to an administration set for delivery to the patient.

There are a variety of examples of drug delivery systems. An example of such a system is disclosed in U.S. Pat. No. 4,850,978. The system includes a cartridge for introducing a beneficial agent into a fluid conduit for delivery of the agent to a patient. The cartridge includes a rigid hollow tube and an agent-containing chamber slidably mounted at least partially within the tube. In a first, pre-use, position, the chamber extends farther from the hollow tube than it does in a second position. A cannula is mounted to the hollow tube extending opposite the chamber. When the chamber is in the second position, the cannula pierces a closure means creating a fluid flow path.

U.S. Pat. No. 4,804,366 also discloses a drug delivery system including an adaptor having an improved flow path means providing both an inlet and an outlet to the agent-containing chamber of a cartridge. The cartridge and adaptor permit a single opening through the injection sites at opposite ends of the flow path means, while still permitting simultaneous flow both into and out of the chamber. An adaptor and a cartridge is provided including a rigid cannula with an inlet and an outlet and a shell substantially coaxial and spaced from the cannula intermediate of the cannula inlet and the cannula outlet, so that the shell of the cannula defines a channel therebetween. Both the cannula inlet and the cannula outlet are adaptable to form a single piercing opening in a resilient injection site associated with the receptacle of the delivery system. Both the channel outlet and channel inlet are adapted to form a single piercing opening in a resilient injection site associated with the cartridge.

The two above described systems provide automatic systems for drug delivery and reconstituting a drug. Manual devices that can be used for reconstituting a drug in a vial do not typically have the same concerns that are faced in automatic systems, such as those described above. Typically, in manual systems, the cannula is used to infuse liquid and a separate member is used to vent air as disclosed in U.S. Pat. No. 4,537,593. High pressure and high velocity diluent is passed through the cannula for a short period of time. The vials, after the diluent is injected, are typically manually agitated prior to complete drug dissolution. Pressure differential between the vial contents and the syringe barrel drive the mixture into the syringe. The user can pull a vacuum in the syringe barrel.

A number of concerns and requirements are raised in automatic systems that are not typically present in such manual systems.

Aside from coring problems, a pointed cannula, for being received within a septum in an automatic system that closes a vial containing a powdered drug, may have other disadvantages. When the pointed cannula is inserted into the vial, the powdered drug can be received within the pointed cannula plugging the cannula and preventing fluid flow therethrough. This, however, must be contrasted with the need for an opening that allows the maximum amount of air is displaced as the vial fills. This condition dictates that the cannula opening is located as close as possible to the distal end of the cannula.

In a reconstitution device, fluid passing through the drug bed by means of an inlet and an outlet at opposite ends of the vial erode the drug. Dissolution of the drug is correlated to fluid volume throughput. Due to the low operating system pressure and delivery rates of automatic systems, it is important that restrictions are not created through the outlet of the cannula that impede fluid flow.

A further requirement with respect to drug delivery or reconstitution devices is the need to maintain the integrity of the system. It is therefore important to maintain a closed system during vial inactivation, i.e., when the cannula pierces the septum.

Furthermore, unlike manual reconstitution devices, automatic reconstitution devices require a different set of flow conditions. Partially dissolved clumps of drugs must be restricted from entering the cannula lumen during the dissolution process. If particles enter the lumen this can result in blockage of the lumen and nonuniform drug delivery profiles or complete failure.

SUMMARY OF THE INVENTION

The present invention provides an improved cannula that can be used to reconstitute powdered drugs in a drug delivery system. Furthermore, the present invention provides a cannula, and drug delivery system incorporating same.

To this end, the present invention provides a cannula structure for use in a reconstitution device for reconstituting a powdered drug comprising a cannula having a first end and a second end, and defining a channel in an interior thereof between the first and second ends. The first end is closed and includes a member for piercing a septum. The cannula includes at least two slots providing fluid communication between the channel and an exterior of the cannula. The slots are located in juxtaposition to the first end and have a width, as measured along a length of the cannula, that is less than a length of the slots, as measured around the cannula. The slots also have a minimum projected area equal to or greater than the cross-sectional area of the channel.

In an embodiment of the invention, the length of the slots extends for approximately one half the outer circumference of the cannula.

In an embodiment of the invention, the distance between a leading edge of a first slot and a distal edge of a last slot is less than the thickness of a septum designed to receive the cannula.

In an embodiment of the invention, the second end of the cannula is blunt.

In an embodiment of the invention, at least one of the slots has a rectangular cross-sectional shape.

In an embodiment of the invention, the slots have substantially the same shape.

In an embodiment, the present invention provides a cartridge for introducing a beneficial agent into a fluid conduit for delivery of the beneficial agent. The cartridge comprises a rigid hollow tube. A chamber having a septum and housing an at least partially solid beneficial agent therein is mounted adjacent a first end of the hollow tube and is slidably mounted at least partially within the hollow tube from a first position to a second position, such that in the first position the chamber extends a greater distance from the hollow tube than in the second position. A cannula is mounted in the hollow tube and includes a first end and a second end. The first end has a closed end for piercing the septum. The cannula includes a channel located between the first and second end. Additionally, the cannula includes at least two slots providing fluid communication between an exterior of the channel and the channel, the slots being located in juxtaposition to the pointed first end and having a total surface area that is at least equal to the cross-sectional surface area of the channel. The length of the cannula occupied by the slots is less than or equal to the width of the septum to insure a closed system.

In an embodiment of the invention, a rigid shell circumscribes a portion of the cannula and defines a channel between an outer wall of the cannula and an inner wall of the rigid shell.

An advantage of the present invention is that it provides a non-coring cannula that can be used in a drug delivery device.

A further advantage of the present invention is that it provides a cannula that can be used to reconstitute powdered drugs and will not become clogged or plugged with the powdered drug during the activation process.

Additionally, an advantage of the present invention is that it provides a non-coring cannula, but at the same time, does not create fluid flow restrictions that impede flow rate even at low operating system pressure and delivery rates.

Moreover, an advantage of the present invention is that the cannula, in use in a drug delivery system, allows the device to maintain a closed system.

Still further, an advantage of the present invention is that the cannula prevents particles from entering the lumen of the cannula.

Additional features and advantages of the present invention are described in, and will be apparent from, the detailed description of the presently preferred embodiments and from the drawings.

BRIEF DESCRIPTION OF THE DRAWINGS

FIG. 3 illustrates a perspective view of the improved cannula of the present invention.

FIG. 4 illustrates an enlarged view of a portion of the embodiment of the cannula illustrated in FIG. 3.

FIG. 5 illustrates, graphically, data generated in the experiment disclosed in the example.

FIG. 6 illustrates, graphically, further data generated in the experiment disclosed in the example.

DETAILED DESCRIPTION OF THE PRESENTLY PREFERRED EMBODIMENTS

The present invention provides an improved cannula that can be used for reconstituting drugs. Although, in the embodiment illustrated, preferably, the cannula is used for reconstituting or diluting drugs in a drug delivery system, the cannula can be used for other applications. Moreover, the present invention provides an improved drug delivery device including the cannula of the present invention.

Figure 1:
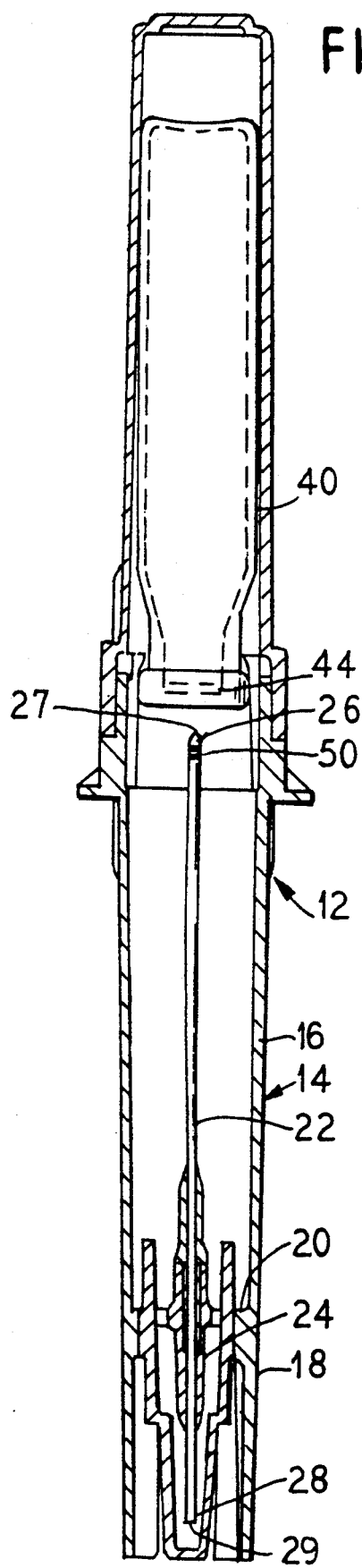
FIG. 1 illustrates a cross-sectional perspective view of an in-line device including the improved cannula of the present invention.
Figure 2:
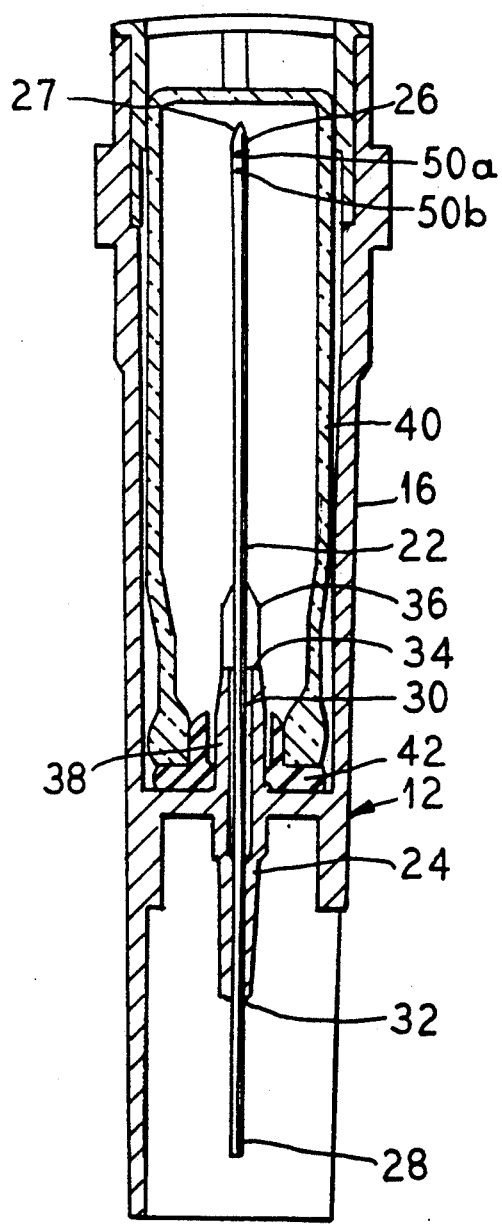
FIG. 2 illustrates a cross-sectional perspective view of an in-line device, including the improved cannula of the present invention, when the device is in an activated state.

Referring now to FIGS. 1 and 2, there is illustrated an in-line device, or cartridge, that is designed to be coupled to an IV set. The cartridge can be substantially similar to that disclosed in U.S. Pat. No. 4,804,366, the disclosure of which is incorporated herein by reference.

Briefly, the cartridge 12 includes an adaptor 14 having a rigid hollow cylinder tube means 16 and a keyway wall 18, with the keyway wall 18 being part of the tube 16. A plate 20 is mounted across the tube 16 and defines the starting point for the keyway wall 18. The improved cannula 22 of the present invention extends through the plate 20; the improved cannula 22 will be discussed in more detail infra.

A generally cylindrical shell 24 extends from both sides of the plate 20. The hollow tube 16, the plate 20, and the shell 24 may be formed as a single piece of the same material, such as a plastic.

The shell 24 is spaced from the cannula 22 with the shell 24 encompassing the cannula 22, but, being shorter than either end of the cannula 22. The cannula 22 includes a first end 26 and a second end 28. As discussed in more detail below, the first end 26 terminates in a closed pointed member 27. The second end 28 includes an outlet 29, and in the embodiment illustrated, is preferably blunt. However, if desired, a pointed cannula can be utilized at the second end 28. Furthermore, if desired, the blunt end 28 can be covered by a sheath such as that disclosed in U.S. patent application Ser. No. 07/573,529 filed on Aug. 27, 1990 now U.S. Pat. No. 5,167,642 entitled: "SHEATH FOR A CANNULA", the disclosure of which is incorporated herein by reference.

The shell 24 is intermediate of the first and second end 26 and 28, respectively, of the cannula 22. The cannula 22 and shell 24 define a channel 30 therebetween. In a preferred embodiment, the periphery of the cannula 22 is circular along its length. Similarly, the internal surface of the cannula 22 is preferably circular along its length.

The channel 30 includes a channel inlet 32 defined between the shell 24 and the cannula 22, short of the cannula outlet 29 at the second end 28. Similarly, the channel 30 includes a channel outlet 34 defined by the shell 24 and the cannula 22, short of the first end 26 of the cannula.

A preferably plastic cannula holder 36 is secured to the cannula 22. The cannula holder 36 grips the cannula 22. Extension means 38 extend between the cannula holder 36 and the shell 24, across the channel 30 thereby securing the cannula 22 relative to the shell 26. In the illustrated embodiment, the extension means 38 is part of the holder 36.

The cannula 22 is secured to the shell 24 while still maintaining an open flow path through the channel inlet 32, the channel 30, and the channel outlet 34. Thus, a very small flow path is created outside a single cannula 22, with precision.

The cartridge 12 further includes a tubular chamber 40 containing the beneficial agent such as a dry powdered drug. In an embodiment, the tubular chamber 40 is a glass vial. A pierceable stopper 42 or other closure means closes the tubular chamber 40.

The shell 24, along with the channel outlet 34 and the first end of the cannula 26 are designed to pierce the pierceable stopper 42, or other injection site/closure means, of the chamber 40 having the beneficial agent therein. The pierceable stopper 42 is mounted within the mouth 44 of the tubular chamber 40. The rubber stopper 42 may be secured within the tubular chamber 40 by means of a metal band around the periphery of the mouth and the rubber stopper in a known manner for securing a stopper in a standard drug vial. The tubular chamber 40 is slidably mounted within the rigid cylinder such that the rubber stopper 42 faces the plate 20. In place of the pierceable stopper 42, other pierceable closure means can be provided.

When the chamber 40 is in the first position, the rubber stopper 42 has not been pierced by either the shell or the first end 26 of the cannula 22. The pierceable stopper 42 remains spaced from the cannula 22 when the cartridge 40 is in the first position.

As illustrated, pursuant to the present invention, the first end 26 of the cannula 22 includes a closed pointed end 27. The closed pointed end 27 is designed to pierce the rubber stopper 42.

As illustrated in FIGS. 3 and 4, to provide fluid communication between the second end 28 of the cannula 22 through the lumen or channel of the cannula, at a first end 26 of the cannula, the cannula 22 includes slots 50. In the preferred embodiment illustrated, two slots 50a and 50b are provided. However, more than two slots can be utilized.

What is important is that due to the low operating system pressure and delivery rates of the automatic system, a flow rate restriction is not created through the flow path. To this end, the cannula 22 and slots 50a and b at the first end 26 are designed to have a minimum projected area that is equal to or greater than the cross-sectional area of the cannula lumen. Therefore, the surface area defined by the slots 50a and b is as great or greater than the cross-sectional surface area of the lumen or channel. Accordingly, fluid can flow through the lumen from a second end 28 through the slots 50a and b, and vice versa, without the flow rate being impeded.

However, slots 50a and b individually have a maximum surface area that is less than the cross-sectional surface area of the lumen or channel. This prevents blockage in the lumen.

As illustrated in FIGS. 3 and 4, the slots 50a and b are constructed so that they have a width with respect to the length as measured in direction of the cannula 22 that is less than a length of the slots 50a and b with respect to a circumference of the cannula 22. In a preferred embodiment illustrated, the slots 50a and b have a substantially rectangular shape cross-sectional shape. This shape serves a number of purposes. At the outset, the shape of the slots 50a and b is designed so that clumps of particles cannot be received within the slots 50a and b and thereby block the lumen.

Furthermore, the slots 50a and b are constructed so that a distance "D", the distance from the leading edge 51 of the first slot 50a to the trailing edge 53 of the last slot 50b, is less than or equal to the width of the rubber stopper 42. This insures that a closed system is provided during activation of the device.

Due to the closed end 27 of the cannula 22, a non-coring cannula is provided. Furthermore, the cannula 22 will not become packed or filled with the powdered drug during the activation process. As set forth in detail below, pursuant to the present invention, vial priming time and variations of priming times are significantly improved.

As illustrated, the slots 50a and b are located immediately in juxtaposition to the closed end 27 of the cannula 22. This locates the slot openings 50a and b as close as possible to the distal (first) end 26 of the cannula 22 and provides optimum operating conditions for the displacement of air as the vial 40 fills. In this regard, it should be noted that in the embodiment of the device 10 illustrated in FIGS. 1 and 2, the cannula 22 initially serves to allow air to be vented from the vial 40 while liquid passes into the vial 40 through channel 30.

In a preferred embodiment that has been found to function satisfactorily, the cannula 22 is constructed so that distance "A" is preferably 0.086 inches, distance "B" is preferably 0.021 inches, distance "C" is preferably 0.013 inches, and distance "D" is preferably 0.041 inches. In the illustrated preferred embodiment, the angle $\alpha$ is preferably 45 degrees.

In constructing a cannula 22 in accordance with the present invention, it is important that the cannula be burr-free, oil-less (clean) machined. One method of manufacturing the cannula 22 that has been found to function satisfactorily is a process known as "Water bath wire E.D.M." This process allows clean, accurate, and economical machining.

By way of example, and not limitation, an example of the present invention will now be given.

The present invention was evaluated, using ampicillin sodium units was evaluated, in terms of vial prime time, cannula design. It was found that the current bevelled (pointed open) cannula design had a prime time of $118\pm68$ seconds (avg. $\pm$ std. dev.). The present invention with slots had a prime time of $27\pm9$ seconds. This study concludes that the slotted closed end cannula provides better system performance than the current bevelled needle design with respect to absolute prime time and prime time variation. This testing also concluded that there was no significant difference between packing at the glass or stopper end of the vial based on vial prime time with the present invention.

Partial and complete flow blockage had been observed using ampicillin sodium devices with a bevelled cannula tip. Powder packing in bevelled cannula tips was observed in nafcillin sodium flow blockage. The purpose of this analysis was to evaluate slots in a closed end cannula as an alternative to the current design with respect to vial prime time. Long cartridge prime times can be perceived by the user as device stop flows. A reduced prime time would provide less perceived stop flows.

Test Articles

Ampicillin sodium, 1 gram, in MainStream TM vials, available from Baxter Healthcare Corporation. Two types of MainStream TM devices were used:
Closed end slotted needle cartridges (made pursuant to the present invention)
Normal bevelled needle cartridges Test System Ampicillin sodium, 1 gram, in MainStream TM vials were assembled. The vials were then tapped 300 times on a Quantachrome Dual Autotap at either the stopper end or the glass end. Tapping 300 times simulates "worst case" transportation conditions.

The tapped vials were activated onto MainStream TM cartridges using the present invention or normal bevelled needle. The cartridges were docked on solutions sets of D5W with a 30 inch head height and 20 gauge needle at the end. The roller clamp was fully open but a hemostat was used to clamp the tubing until a stop watch was started. The time was recorded when the first drop entered the drip chamber. Slotted cannula cartridges were allowed to flow for 15 minutes after the first drop.

| Experimental design Mainstream TM Vials | | | |
|---|---|---|---|
| Slotted Cannula tapping | | Standard Bevel tapping | |
| glass | stopper | glass | stopper |
| 25 units | 25 units | 18 units | 18 units |
| glass end | stoooer end | | |

TABLE 1

| Test for Effect of packing with slotted cannula design. | | |
|---|---|---|
| | glass end | stopper end |
| Sample size | 25 | 25 |
| Mean | 28.48 | 26.4 diff. = 2.08 |
| Std. deviation | 11.435 | 6.32456 |

The above statistics (Table 1.) compares the 25 unit's prime time for tapping at the glass end to the 25 unit's prime time for tapping at the stopper end. This data is illustrated graphically in FIG. 4. Analysis of the data indicates no significant difference between the variances of the two tapping methods. Therefore, the means may be compared. Using the two 95% confidence intervals for the difference in the means, this difference lies somewhere between 3.21343 and 7.37343.

TABLE 2

| Test for effect of packing on bevelled cannula design. | | |
|---|---|---|
| | glass end | stopper end |
| Sample size | 18 | 18 |
| Mean | 101.389 | 133.889 diff. = 32.5 |
| Std. deviation | 72.3668 | 61.1651 |

The above statistics (Table 2.) compares the 18 unit's prime time for tapping at the glass end to the 18 unit's prime time for tapping at the stopper end. This data is graphed in FIG. 5. Analysis of the data indicates no significant difference between the variances of the two tapping methods. Therefore, the means may be compared. Using the two 95% confidence intervals for the difference in the means, this difference lies somewhere between −77.8872 and 12.8872.

TABLE 3

| Combined analysis of bevelled and slotted closed end: | | |
|---|---|---|
| | Bevel | Sidehole |
| Sample size | 36 | 50 |
| Mean | 117.639 | 27.44 diff. = 90.1989 |
| Std. deviation | 68.0618 | 9.2055 |

The above statistics (Table 3.) compares the 36 unit's prime time for bevelled cannula to the 50 unit's prime time for slotted cannulas. Analysis of the data indicates no significant difference between the variances of the two tapping methods. Therefore, the means may be compared. Using the two 95% confidence intervals for the difference in the means, this difference lies somewhere between 67.0402 and 113.358. Since the value 0.0 is not within this interval, there is a statistically significant difference between the means at the 95% confidence level.

Conclusions

This study concludes that a slotted closed end cannula provides better system performance, with respect to vial prime time, than the current bevelled needle design. There is a statistically significant lower mean prime time for the slotted closed end cannula (27 seconds versus 118 seconds for the bevelled needle). Long vial prime times can be perceived by the user as device stop flows. A reduced prime time would provide less perceived stop flows.

The standard deviation of the prime time is also reduced from 68 seconds with the bevelled needle to 9 seconds with the slotted closed end cannula. A reduced variation in prime time may also provide a reduced variability in drug delivery.

Tapping ampicillin vials 300 times has been observed to be a maximum packing condition. This experiment also concludes that there is no significant difference between vials packed at the glass or stopper end of the vial. An extension of this conclusion may be that shipping orientation does not cause significant differences in vial prime time.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A cannula structure for use in a reconstitution device for reconstituting a powdered drug comprising:
a cannula having a first end and a second end, and defining a channel in an interior thereof between the first and second ends, the first end being closed and including a member for piercing a septum, the cannula including at least two slots providing fluid communication between the channel and an exterior of the cannula, the slots being located in juxtaposition to the first end, the slots having a width, as measured along a length of the cannula, that is less than a length of the slots, as measured around the cannula, the slots having a total minimum projected area equal to or greater than the cross-sectional area of the channel.

2. The cannula of claim 1 wherein the length of the slots extends for approximately one half the outer circumference of the cannula.

3. The cannula of claim 1 wherein the distance between a leading edge of a first slot and a distal edge of a last slot is less than the thickness of a septum designed to receive the cannula.

4. The cannula of claim 1 wherein the second end of the cannula is blunt.

5. The cannula of claim 1 wherein at least one of the slots has a rectangular cross-sectional shape.

6. The cannula of claim 1 wherein the slots have substantially the same shape.

7. The cannula of claim 1 wherein the cannula is constructed from stainless steel.

8. The cannula of claim 1 wherein the individual projected area of each slot is less than the cross-sectional area of the channel.

9. A cannula for use in a device for reconstituting a powdered drug comprising:
a first and a second end;
a channel located between the first and second ends;
the first end including a pointed closed end for piercing a septum;
at least two slots located in juxtaposition to the pointed closed end and providing fluid communication between the exterior of the channel and the channel, the total surface area of the slots being equal to or greater than the cross-sectional surface area of the channel and the distance from a leading edge of a first slot to a trailing edge of a last slot being less than or equal to a width of the septum so as to insure a closed system when the cannula pierces the septum.

10. The cannula of claim 9 wherein the slots extend for approximately one half the outer circumference of the cannula.

11. The cannula of claim 9 wherein the second end of the cannula is blunt.

12. The cannula of claim 9 wherein at least one of the slots has a substantially rectangular cross-sectional shape.

13. The cannula of claim 9 wherein the slots have substantially the same shape.

14. The cannula of claim 9 wherein the cannula is constructed from stainless steel.

15. The cannula of claim 9 wherein the surface area of the individual slots is less than the cross-sectional surface area of the channel.

16. A cartridge for introducing a beneficial agent into a fluid conduit for delivery of the beneficial agent, the cartridge comprising:
a rigid hollow tube;
septum and housing an at least partially solid beneficial agent therein, the chamber being mounted adjacent a first end of the hollow tube and being slidably mounted at least partially within the hollow tube from a first position to a second position, such that in the first position the chamber extends a greater distance from the hollow tube than in the second position; and
a cannula mounted in the hollow tube, including a first end and a second end, the first end having a closed end for piercing the septum, a channel located between the first and second end, the cannula including at least two slots providing fluid communication between an exterior of the channel and the channel, located in juxtaposition to the pointed first end and having a total surface area at least equal to the cross-sectional surface area of the channel, the length of the cannula occupied by the slots being less than or equal to the width of the septum to insure a closed system.

17. The cartridge of claim 16 including a rigid shell circumscribing a portion of the cannula and defining a channel between an outer wall of the cannula and an inner wall of the rigid shell.

18. The cartridge of claim 16 wherein the slots have a substantially rectangular cross-sectional shape.

19. The cartridge of claim 16 wherein the second end of the cannula is blunt.

20. The cartridge of claim 16 wherein the slots have substantially the same shape.

21. The cartridge of claim 17 wherein the shell is designed to pierce the septum when the chamber is moved to a second position.

22. The cartridge of claim 16 wherein the slots have a width, as measured along a length of the cannula, that is less than the length of the slots.

23. The cartridge of claim 16 wherein the surface area of the individual slots is less than the cross-sectional surface are of the channel.

* * * * *

UNITED STATES PATENT AND TRADEMARK OFFICE
CERTIFICATE OF CORRECTION

PATENT NO. : 5,226,900
DATED : July 13, 1993
INVENTOR(S) : Joseph A. Bancsi et al.

It is certified that error appears in the above-identified patent and that said Letters Patent is hereby corrected as shown below:

In column 10, line 15, before "septum" insert --a chamber having a--.

Signed and Sealed this

Twenty-second Day of February, 1994

Attest:

BRUCE LEHMAN

Attesting Officer        Commissioner of Patents and Trademarks